United States Patent [19]

Tedder

[11] 4,424,361
[45] Jan. 3, 1984

[54] PROCESS FOR PREPARING POLYCYCLIC TRIAZOLES USED TO INHIBIT ALLERGIC RESPONSES

[75] Inventor: John M. Tedder, Redhill, England
[73] Assignee: Beecham Group Limited, England
[21] Appl. No.: 224,954
[22] Filed: Jan. 14, 1981
[30] Foreign Application Priority Data Jan. 23, 1980 [GB] United Kingdom ............. 8002328

[51] Int. Cl.$^3$ ........................................... C07D 249/22
[52] U.S. Cl. ................................................. 548/259
[58] Field of Search ..................................... 548/259

[56] References Cited

U.S. PATENT DOCUMENTS 4,263,309  4/1981  Buckle et al. .................. 424/269

OTHER PUBLICATIONS

Fieser and Martin, "Comparison of Heterocyctic Systems with Benzene", *J. of Am. Chem. Soc.*, V 57, p. 1844 (1935).
Thielhiemer, W., *Synthetic Method of Organic Chemistry*, vol. 15, No. 26 (1961).
Patchornik, Abraham, "Carbobenzoxy Derivatives of Histidine, Imidazole, and Benzimidazole", *J. of Am. Chem. Soc.*, vol. 79, pp. 6416–6420, (1957).
McOmie, J. F. W., *Protective Groups in Organic Chemistry*, p. 408, (1973).
Kross and Meienhoffer, *The Peptide*, p. 77, (1981).
Rao et al., "Thermal Debenzylation ... " *Chem. Abst.*, 89:24243v, 1978.
Fuji et al., "Hard Acid and Soft Neucleophile System," *Chem. Abst.* 90:202998 (1979).
Fawali et al., "Solvolysis N–Benzylarylsulfonamides ... ." *Chem. Abst.* 95:149489k, (1981).
Kiso, et al., "Efficien ... Push-Pull Mechanism" *Chem. Abst.* 93:47172t, (1980).

Primary Examiner—Donald G. Daus
Assistant Examiner—G. Hendricks
Attorney, Agent, or Firm—Jacobs & Jacobs

[57] ABSTRACT

Process for the preparation of compounds of the formula (I):

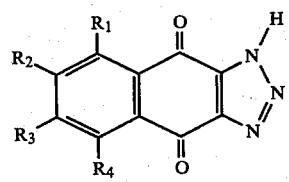

and pharmaceutically acceptable salts thereof wherein $R_1$, $R_2$, $R_3$ and $R_4$ which may be the same or different, represent hydrogen, halogen, nitro, lower alkyl or lower alkoxy, where lower means of up to six carbon atoms, or any adjacent two of $R_1$ to $R_4$ taken together represent an alkylene group containing from 3 to 5 carbon atoms or a 1,4-buta-1,3-dienylene group, by removal of $CH_2R_5$ wherein $R_5$ is phenyl optionally substituted with one or two groups selected from $C_{1-4}$ alkyl, $C_{1-4}$ alkoxy, halogen or nitro from a compound of formula (II):

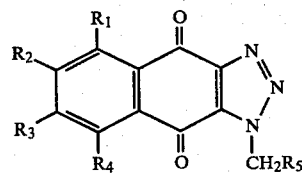

with an alkali metal $C_{1-4}$ primary alkoxide. The compounds are used to inhibit allergic responses.

5 Claims, No Drawings

PROCESS FOR PREPARING POLYCYCLIC TRIAZOLES USED TO INHIBIT ALLERGIC RESPONSES

This invention provides a process for the preparation of anti-allergy triazoles.

European Patent Application No. 78300485.6 published June 13, 1979 and allowed U.S. patent application Ser. No. 953,464 now U.S. Pat. No. 4,263,309 disclose that compounds of the formula (I):

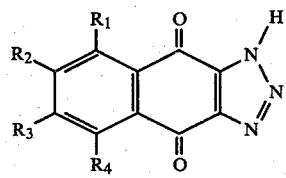

and pharmaceutically acceptable salts thereof wherein $R_1$, $R_2$, $R_3$ and $R_4$ which may be the same or different, represent hydrogen, halogen, nitro, lower alkyl or lower alkoxy, where lower means of up to six carbon atoms, or any adjacent two of $R_1$ to $R_4$ taken together represent an alkylene group containing from 3 to 5 carbon atoms or a 1,4-buta-1,3-dienylene group, are of value in the prophylaxis of diseases in which the symptoms are controlled by mediators of the allergic response. Examples of such diseases include bronchial asthma, rhinitis, hayfever, and allergic eczema.

These European and U.S. Patent Applications also describe a process for the preparation of the compounds of the formula (I).

A new process for the preparation of the compounds of the formula (I) has now been discovered.

Accordingly the present invention provides a process for the preparation of a compound of the formula (I), or a pharmaceutically acceptable salt thereof, which process comprises reacting a compound of formula (II):

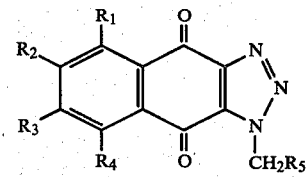

wherein $R_5$ is phenyl optionally substituted with one or two groups selected from $C_{1-4}$ alkyl, $C_{1-4}$ alkoxy, halogen or nitro and the remaining variables are as defined in formula (I) with an alkali metal $C_{1-4}$ primary alkoxide.

One process of the present invention uses compounds of the formula (II) wherein $R_5$ is phenyl.

Suitable $R_5$ include phenyl, 4-methylphenyl, 4-methoxyphenyl, 4-chlorophenyl and 4-nitrophenyl. A preferred value for $R_5$ is 4-methoxyphenyl.

Suitable examples of alkali metal $C_{1-4}$ primary alkoxides to use in this reaction include sodium methoxide and ethoxide, preferably the methoxide.

The reaction is carried out in a suitable solvent often the corresponding primary alcohol. By way of example with sodium methoxide, suitably a solution of sodium methoxide in methanol is added to a solution of the Compound (II) in N,N-dimethylformamide, followed by warming the solution to 40°–50° C. for typically 5–30 minutes (until it has gone yellow).

The reaction will form the corresponding alkali metal salt which may be acidified to give the free compound of the formula (I).

Compounds of the formula (II), which as novel intermediates form an important part of this invention, may be prepared by reacting a compound of the formula (III):

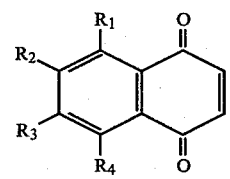

with an azide $R_5CH_2N_3$.

This reaction is conveniently carried out by reaction of the compound of formula (III) with the azide at temperatures between 30° and 80°, preferably 50°, in a suitable organic solvent such as N,N-dimethylformamide (DMF), ethyl acetate or toluene. Preferably DMF is the solvent, more preferably ethyl acetate. The reaction time is dependent on the solvent and temperature but is usually in the order of 3–24 hours.

With unsymmetrical quinones a mixture of N-1 and N-3 benzyl naphthotriazoles will usually be formed. These may be separated by conventional techniques such as column chromatography if desired or deprotected as a mixture to give a single N—H naphthotriazole as a common product.

It will be appreciated that although it is believed that the process of this invention is applicable to the preparation of any compound of the formula (I), it will be especially useful in the preparation of compounds of the formula (I) that are stated in the European and U.S. Patent Applications to be of particular interest.

Such compounds are as follows:

One group is that in which at least one of $R_1$ to $R_4$ is hydrogen and the remainder are as previously defined. An example of such a compound is 4,9-dihydro-6,7-dimethyl-5-nitro-4,9-dioxo-1H-naphtho-[2,3-d]-triazole.

A further group is one where two of $R_1$ to $R_4$ are hydrogen and the remainder are as previously defined. An example of such a compound is 4,9-dihydro-5,6-dimethyl-4,9-dioxo-1H-naphtho-[2,3-d]-triazole. One preferred sub-group of compounds of formula (I) is that in which $R_1$ and $R_4$ are hydrogen and $R_2$ and $R_3$, which may be the same or different, represent methyl, ethyl or n-propyl.

In the European and U.S. Patent Applications the compound 4,9-dihydro-6,7-dimethyl-4,9-dioxo-1H-naphtho[2,3-d]-v-triazole, and its salts—especially its sodium salt—is highlighted. In a preferred embodiment of this invention the process is adapted for the preparation of this compound, or of its salts. This adaptation is readily achieved by use of a compound of formula (II) wherein $R_1$ and $R_4$ are hydrogen, and $R_2$ and $R_3$ are both methyl.

As disclosed in the European and U.S. Patent Applications, the triazole moeity of the compounds of formula (I) has an acidic hydrogen, and accordingly may form salts, including pharmaceutically acceptable salts. Such salts include aluminium, alkali metal and alkaline earth metal salts such as the sodium, potassium and magnesium salt; and salts with organic bases such as amines or amino compounds including physiologically active amines such as (−) ephedrine. The sodium and (−) ephedrine salts are preferred.

Salts may be made by conventionally reacting the compound of the formula (I) with the relevant metal or oxide or a base or basic salt thereof as appropriate or with the relevant base as appropriate. Salts may be interconverted by passage through a suitable ion-exchange column.

The following Examples illustrate the invention.
All temperatures are in degrees Celsius.

EXAMPLE 1

(a) 1-Benzyl-4,9-dihydro-6,7-dimethyl-4,9-dioxonaphtho[2,3-d]-v-triazole 6,7-Dimethylnaphtho-1,4-quinone (2.0 g, 0.0108 mole) and benzyl azide (0.65 g, 0.0049 mole) in DMF (20 ml) were stirred at 50° C. for 17 hours. The mixture was cooled and poured into water (400 ml). The cream precipitate was filtered off, washed with water (2×50 ml) and dried to yield 1.80 g of beige solid, which after tituration with boiling petrol (60°–80°, 3×100 ml) gave the required 1-benzyl-4,9-dihydro-6,7-dimethyl-4,9-dioxonaphtho[2,3-d]-v-triazole (0.941 g, 60.6%, mpt 193°–8°). Recrystallization from ethyl acetate gave pale yellow needles of mpt 200°–1°. Analysis (Calculated: C, 71.91; H, 4.76; N, 13.32. Found: C, 71.88; H, 4.36; N, 13.00); Nmr δ(CDCl$_3$) 2.4 (6H, s, CH$_3$); 6.0 (2H, s, CH$_2$), 7.4 (5H, m, Ph); 7.95 (1H, s); 8.05 (1H, s); Ir $\nu_{max}$1695 cm$^{-1}$; Uv $\lambda_{max}$260 nm, E$_m$=33,400.

(b) 4,9-Dihydro-6,7-dimethyl-4,9-dioxo-1H-naphtho[2,3-d]-v-triazole

1-Benzyl-4,9-dihydro-6,7-dimethyl-4,9-dioxonaphtho[2,3-d]-v-triazole (0.176 g, 0.00055 mole) was dissolved in DMF (20 ml) and treated with a methanolic solution of sodium methoxide (from sodium, 0.070 g, 0.003 mole, and methanol 5 ml). A red colour was observed which rapidly changed to black. The solution was warmed to 50° with swirling when it became dark green and finally yellow-red after 30 minutes. After a further 30 minutes the mixture was poured into water (100 ml) and the red solution washed with ethyl acetate (2×25 ml). The aqueous phase was then acidified to pH 1 with concentrated hydrochloric acid when a cream solid precipitated. This was filtered off and washed with water (2×5 ml). After drying a yield of 0.090 g (70%) of the title compound was obtained as its monohydrate (mpt 252°–8° d authentic material melts at 262° d, other physical characteristics identical.) c.f. EP 78300485.6 and U.S. Ser. No. 953,464.

EXAMPLE 2

(a) 1-Benzyl-4,9-dihydro-4,9-dioxonaphtho[2,3-d]-v-triazole

Naphtho-1,4-quinone (4.74 g, 0.03 mole) and benzyl azide (1.33 g, 0.01 mole) were dissolved in DMF (20 ml) and the solution stirred and heated to 80° for 18 hours. The mixture was then cooled and the DMF removed using a rotary evaporator. The residue was extracted with light petrol (3×25 ml) to remove excess naphthoquinone. The insoluble residue was recrystallized from ethyl acetate to yield pale yellow crystals of the title compound (mpt 243°; Analysis, calculated: C, 71.91; H, 4.76; N, 13.32. Found: C, 71.88; H, 4.62; N, 13.14: Nmr: δ(CDCl$_3$) 6.06, (2H, s, CH$_2$); 7.3 (5H, m, Ph), 7.8 (2H, m), 8.3 (2H, m).

(b) 4,9-Dihydro-4,9-dioxo-1H-naphtho[2,3-d]-v-triazole

1-Benzyl-4,9-dihydro-4,9-dioxonaphtho[2,3-d]-v-triazole (0.100 g, 0.000346 mole) was dissolved in DMF (25 ml) and treated with a methanolic solution of sodium methoxide (from methanol, 5 ml and sodium 0.028 g, 0.0012 mole). The mixture became dark and was warmed to 50° with swirling. After 45 minutes at this temperature the mixture had become red-yellow. After cooling the DMF was evaporated, in vacuo, and the residue was dissolved in water (25 ml). The resulting solution was washed with ethyl acetate (3×10 ml) and the aqueous phase acidified to pH 1 with concentrated hydrochloric acid, when a precipitate formed. This was filtered off, washed with water (3×5 ml), sucked dry and recrystallized from acetone/water to yield 0.021 g, (31.0%) of the title compound as its monohydrate of mp. 250° dec (physical data identical with authentic material. c.f. EP 78300485.6 or U.S. Ser. No. 953,464.

EXAMPLE 3

(a) 1- and 3-Benzyl-4,9-dihydro-4,9-dioxo-6-methylnaphtho[2,3-d]-v-triazole

6-Methylnaphthoquinone (3.84 g, 0.022 mole) and benzyl azide (1.0 g, 0.0074 mole) were dissolved in N,N-dimethylformamide (40 ml) and stirred at 50° for 16 hours. The solvent was removed in vacuo, the residue purified by chromatography on silica eluting with chloroform/light petrol (3:7). Unreacted 6-methylnaphthoquinone was eluted first followed by 1,40 g (62%) of a 1:1 mixture of the N-1 and N-3 benzyl isomers, (as shown by splitting of the Me signal in the 250 MHz NMR), mpt 187°–196° C.

Nmr (CDCl$_3$) 2.5 (3H,s,CH$_3$); 6.0 (2H, s,CH$_2$Ph); 7.2–8.3 (8H,m,aromatic Hs).

Analysis: calculated for C$_{18}$H$_{13}$N$_3$O$_2$; C, 71.28; H, 4.32; N, 13.85; Found: C, 71.01; H, 4.12; N, 13.5%.

(b) 4,9-Dihydro-4,9-dioxo-6-methylnaphtho[2,3-d]-v-triazole

A mixture of the above N-benzyl-4,9-dihydro-4,9-dioxo-6-methylnaphtho[2,3-d]-v-triazoles (1.20 g, 0.0039 mole) was dissolved in N,N-dimethylformamide (100 ml) and treated with sodium methoxide (0.648 g, 0.012 mole). The mixture was stirred and heated to 50°. After three hours the solvent was removed in vacuo and the residue partitioned between ethyl acetate (150 ml) and water (150 ml). The aqueous phase was separated and acidified to pH 1 with hydrochloric acid. The precipitated solid was filtered off, dried and chromatographed on silica eluting with ethyl acetate-light petroleum (1:1) to give 0.37 g (45%) of the title compound of mp (CHCl$_3$/petrol) 215° (dec), Nmr δ(CD$_3$)$_2$CO 2.6 (3H, s, CH$_3$); 4.0 (1H, broad exchangeable s, N—H); 7.6–8.4 (3H, m, aromatic H s). Analysis: Calculated for C$_{11}$H$_7$N$_3$O$_2$.H$_2$O: C, 57.07; H, 3.92; N, 18.27; Found: C, 57.25; H, 3.77; N, 18.00%.

EXAMPLE 4

Deprotection of 1-benzyl-4,9-dihydro-4,9-dioxo-naphtho[2,3-d]-v-triazole with sodium ethoxide 1-Benzyl-4,9-dihydro-4,9-dioxo-naphtho[2,3-d]-v-triazole (2.0 g, 0.0069 mole) was dissolved in N,N-dimethyl-formamide (70 ml) and treated with a solution of sodium ethoxide from sodium (0.063 mg, 0.0274 atom) in ethanol (5 ml). The solution was stirred and heated to 50°–70°. After three hours at this temperature the mixture was cooled and the solvent removed under reduced pressure. The residue was partitioned between water (20 ml) and ethyl acetate (20 ml). The phases were separated and the ethyl acetate extracted with water (1×10 ml). The aqueous extracts were combined, acidified to pH 1 with hydrochloric acid and extracted with ethyl acetate (3×15 ml). The extracts were combined, dried and evaporated to yield 4,9-dihydro-4,9-dioxo-naphtho[2,3-d]-v-triazole (0.550 g, 39.9%) mpt 248°–50°.

EXAMPLE 5

Deprotection of 4,9-dihydro-6,7-dimethyl-4,9-dioxo-1(4-methoxybenzyl)-naphtho-[2,3-d]-v-triazole with sodium methoxide 4,9-dihydro-6,7-dimethyl-4,9-dioxo-1(4-methoxybenzyl)naphtho[2,3-d]-v-triazole (0.100 g, 0.288 mole) was dissolved in N,N-dimethyl formamide (10 ml) at 30° and sodium methoxide (0.048 g, 0.888 mole) was added in one portion. The mixture was stirred and heated to 50°. After two hours at this temperature the mixture was cooled and the solvent distilled off. The residue was partitioned between ethyl acetate (20 ml) and dilute sodium bicarbonate solution (20 ml). The aqueous layer was separated and washed with ethyl acetate (10 ml). It was then acidified to pH 1 with hydrochloric acid and extracted with ethyl acetate (3.20 ml). The extracts were combined dried and evaporated to yield 4,9-dihydro-6,7-dimethyl-4,9-dioxo-naphtho[2,3-d]-v-triazole (0.049 g, 75.0%) of mpt 261.2° (authentic material melts at 262°; cf EP 78300485.6 or U.S. Ser. No. 953,464).

I claim:

1. A process for the preparation of a triazole of the formula:

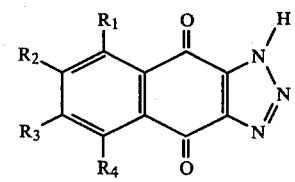

or a pharmaceutically acceptable salt thereof wherein $R_1$, $R_2$, $R_3$ and $R_4$ are the same or different and each is hydrogen, halo, nitro, alkyl of 1 to 6 carbon atoms or alkoxy of 1 to 6 carbon atoms, or any adjacent two of $R_1$ to $R_4$ taken together are an alkylene group of 3 to 5 carbon atoms or 1,4-buta-1,3-dienylene which consists essentially of the steps of (a) allowing a compound of formula

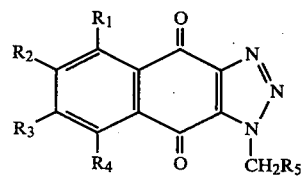

wherein $R_5$ is unsubstituted phenyl or phenyl substituted with one or two members selected from the group consisting of alkyl of 1 to 4 carbon atoms, alkoxy of 1 to 4 carbon atoms, halo and nitro, and $R_1$, $R_2$, $R_3$ and $R_4$ are as herein defined to react with an alkali metal primary alkoxide of 1 to 4 carbon atoms and (b) optionally treating the resulting alkali metal salt with acid to form the free triazole.

2. A process according to claim 1 wherein $R_5$ is phenyl or 4-methoxyphenyl.

3. A process according to claim 2 wherein the alkoxide is sodium methoxide.

4. A process according to claim 3 each of $R_1$ and $R_4$ is hydrogen, and $R_2$ and $R_3$ are the same of different and each is methyl, ethyl or n-propyl.

5. A process according to claim 1 wherein the reaction mixture containing the alkali metal salt of said triazole is rendered acidic to form the free triazole.

* * * * *